(12) United States Patent
Goisis

(10) Patent No.: US 10,960,114 B2
(45) Date of Patent: Mar. 30, 2021

(54) FAT FILTRATION DEVICE

(71) Applicant: Mario Goisis, Milan (IT)

(72) Inventor: Mario Goisis, Milan (IT)

( * ) Notice: Subject to any disclaimer, the term of this patent is extended or adjusted under 35 U.S.C. 154(b) by 338 days.

(21) Appl. No.: 15/766,786

(22) PCT Filed: Oct. 14, 2016

(86) PCT No.: PCT/IB2016/056157
§ 371 (c)(1),
(2) Date: Apr. 6, 2018

(87) PCT Pub. No.: WO2017/064656
PCT Pub. Date: Apr. 20, 2017

(65) Prior Publication Data
US 2018/0303983 A1 Oct. 25, 2018

(30) Foreign Application Priority Data

Oct. 14, 2015 (IT) .................... 102015000061679

(51) Int. Cl.
*A61M 1/02* (2006.01)
*A61M 1/00* (2006.01)
(52) U.S. Cl.
CPC .......... *A61M 1/029* (2013.01); *A61M 1/0056* (2013.01); *A61M 1/02* (2013.01);
(Continued)
(58) Field of Classification Search
None
See application file for complete search history.

(56) References Cited

U.S. PATENT DOCUMENTS 3,705,100 A * 12/1972 Blatt .................. A61M 1/3603
604/6.04
4,753,634 A * 6/1988 Johnson ................. A61B 17/34
210/406
(Continued)

FOREIGN PATENT DOCUMENTS

EP 0495419 A2 7/1992
EP 2452660 A1 5/2012
(Continued)

OTHER PUBLICATIONS

International Search Report and Written Opinion for International Application No. PCT/IB2016/056157 filed Oct. 14, 2016 on behalf of Mario Goisis dated Feb. 20, 2017. 11 pages.

*Primary Examiner* — Robert J Popovics
(74) *Attorney, Agent, or Firm* — Steinfl + Bruno, LLP

(57) ABSTRACT

A device for filtration of fat extracted during liposuction procedures. The device includes: a first reservoir filled with a physiological solution adapted to be suctioned by a syringe containing fat mixed with blood and anesthetic; a second reservoir, empty, intended to receive cyclically from the syringe a liquid mixture consisting of the suctioned solution, blood and anesthetic separated from the fat; and at least one filter element provided with a connection member for connection of the syringe, the filter element being connected to the first reservoir and the second reservoir through a three-way connector. A first one-way valve configured to allow passage of a flow of fluid from the first reservoir towards the connector is arranged on a branch of the connector connected to the first reservoir. A second one-way valve configured to allow passage of a flow of fluid from the connector towards the second reservoir is arranged on a branch of the connector connected to the second reservoir.

12 Claims, 2 Drawing Sheets

(52) U.S. Cl.
CPC ..... *A61M 2202/08* (2013.01); *A61M 2205/75* (2013.01); *A61M 2205/7545* (2013.01)

(56) References Cited

U.S. PATENT DOCUMENTS

| | | | | |
|---|---|---|---|---|
| 5,002,538 A * | 3/1991 | Johnson | A61J 1/2096 | 604/240 |
| 5,052,999 A * | 10/1991 | Klein | A61M 1/0064 | 604/19 |
| 5,328,459 A * | 7/1994 | Laghi | A61M 1/0062 | 128/DIG. 1 |
| 5,352,194 A * | 10/1994 | Greco | A61M 1/008 | 600/579 |
| 5,352,410 A * | 10/1994 | Hansen | A61B 10/007 | 422/419 |
| 5,435,913 A * | 7/1995 | Ashbrook | A61L 2/02 | 210/188 |
| 5,585,007 A * | 12/1996 | Antanavich | A61L 24/106 | 210/500.38 |
| 5,674,394 A * | 10/1997 | Whitmore | A61P 7/04 | 210/321.8 |
| 5,688,244 A * | 11/1997 | Lang | A61M 5/16854 | 200/83 W |
| 5,804,366 A * | 9/1998 | Hu | A61F 2/062 | 435/1.1 |
| 6,010,627 A * | 1/2000 | Hood, III | B01D 63/02 | 210/321.6 |
| 6,020,196 A * | 2/2000 | Hu | A61M 1/00 | 435/283.1 |
| 6,316,247 B1 * | 11/2001 | Katz | A61L 27/3604 | 210/446 |
| 6,342,157 B1 * | 1/2002 | Hood, III | B01D 61/18 | 210/321.6 |
| 6,413,228 B1 * | 7/2002 | Hung | A61B 10/0045 | 600/562 |
| 6,905,612 B2 * | 6/2005 | Dorian | B01D 15/02 | 210/219 |
| 6,953,450 B2 * | 10/2005 | Baldwin | A61M 39/223 | 137/625.23 |
| 7,179,391 B2 * | 2/2007 | Leach | B01D 17/0217 | 210/782 |
| 7,291,450 B2 * | 11/2007 | Sowemimo-Coker | A61K 35/32 | 435/2 |
| 7,374,678 B2 * | 5/2008 | Leach | B01L 3/502 | 210/380.1 |
| 7,694,828 B2 * | 4/2010 | Swift | A61P 43/00 | 210/512.3 |
| 7,713,232 B2 * | 5/2010 | Uber, III | A61J 1/1475 | 604/93.01 |
| 7,758,811 B2 * | 7/2010 | Durack | C12N 5/0612 | 422/73 |
| 7,780,649 B2 * | 8/2010 | Shippert | A61M 1/0056 | 604/542 |
| 7,780,860 B2 * | 8/2010 | Higgins | G01N 33/491 | 210/782 |
| 7,799,569 B2 * | 9/2010 | Durak | C12N 5/0612 | 436/63 |
| 7,832,566 B2 * | 11/2010 | Leach | B01L 3/50215 | 210/380.1 |
| 7,914,689 B2 * | 3/2011 | Higgins | B01L 3/5021 | 210/782 |
| 7,923,203 B2 * | 4/2011 | Sowemimo-Coker | A61K 35/17 | 435/2 |
| 7,943,384 B2 * | 5/2011 | Durack | C12Q 3/00 | 436/63 |
| 8,048,321 B2 * | 11/2011 | Leach | G01N 33/491 | 210/782 |
| 8,062,286 B2 * | 11/2011 | Shippert | A61M 1/0001 | 604/542 |
| 8,133,389 B2 * | 3/2012 | Dorian | B01F 13/0052 | 210/195.2 |
| 8,162,815 B2 * | 4/2012 | Genovesi | A01N 1/02 | 600/36 |
| 8,202,493 B2 * | 6/2012 | Buss | A61M 1/0084 | 422/513 |
| 8,246,947 B2 * | 8/2012 | Hedrick | A61L 27/3834 | 424/93.7 |
| 8,268,171 B2 * | 9/2012 | Liao | C12Q 1/24 | 210/233 |
| 8,308,340 B2 * | 11/2012 | Ferrante | A61B 17/00491 | 366/162.3 |
| 8,366,694 B1 * | 2/2013 | Jordan | C12M 47/04 | 604/319 |
| 8,486,437 B2 * | 7/2013 | Daniloff | A61L 27/54 | 424/423 |
| 8,491,526 B2 * | 7/2013 | Cronin | A61B 17/0057 | 604/82 |
| 8,540,078 B2 * | 9/2013 | Leach | B01D 21/262 | 210/360.1 |
| 8,574,223 B2 * | 11/2013 | Cucin | A61M 1/0058 | 604/542 |
| 8,596,470 B2 * | 12/2013 | Leach | B01L 3/50215 | 210/518 |
| 8,603,346 B2 * | 12/2013 | Leach | B01D 17/12 | 210/789 |
| 8,709,817 B2 * | 4/2014 | Durack | A01N 1/0284 | 436/63 |
| 9,044,547 B2 * | 6/2015 | Tremolada | A61M 5/315 | |
| 9,109,198 B2 * | 8/2015 | Khan | B01F 5/0206 | |
| 9,138,664 B2 * | 9/2015 | Leach | B01D 21/26 | |
| 9,144,583 B2 * | 9/2015 | Ariff | C12M 47/04 | |
| 9,333,447 B2 * | 5/2016 | McKay | B01D 33/0158 | |
| 9,352,021 B2 * | 5/2016 | Hanna | C07K 14/8107 | |
| 9,468,709 B2 * | 10/2016 | Shippert | A61M 1/0009 | |
| 9,480,464 B2 * | 11/2016 | Levine | A61B 10/0283 | |
| 9,604,159 B2 * | 3/2017 | Leach | B04B 3/00 | |
| 9,642,956 B2 * | 5/2017 | Landrigan | A61M 1/029 | |
| 9,700,845 B2 * | 7/2017 | Oranth | B01D 61/18 | |
| 9,744,275 B2 * | 8/2017 | Khouri | A61M 1/0023 | |
| 9,896,722 B2 * | 2/2018 | Link | B03C 5/005 | |
| 10,183,042 B2 * | 1/2019 | Leach | B01L 3/50215 | |
| 10,183,101 B2 * | 1/2019 | Conlan | A61M 1/007 | |
| 10,188,777 B2 * | 1/2019 | Conlan | A61M 1/0009 | |
| 10,213,742 B2 * | 2/2019 | Oranth | B01D 61/22 | |
| 10,279,325 B1 * | 5/2019 | Crombie | B01F 5/0685 | |
| 10,286,128 B2 * | 5/2019 | Wells | A61M 5/484 | |
| 10,286,177 B2 * | 5/2019 | Tremolada | A61K 35/35 | |
| 10,286,178 B2 * | 5/2019 | Tremolada | A61M 5/3286 | |
| 10,300,188 B2 * | 5/2019 | Joos | A61M 1/34 | |
| 10,350,516 B2 * | 7/2019 | Winkler | B01D 27/06 | |
| 10,457,912 B2 * | 10/2019 | Simpson | B01D 21/0012 | |
| 10,478,587 B2 * | 11/2019 | Tremolada | A61M 5/3286 | |
| 10,518,275 B2 * | 12/2019 | Sengun | B01L 3/5021 | |
| 10,588,678 B2 * | 3/2020 | McKay | A61F 2/28 | |
| 10,596,236 B2 * | 3/2020 | Bare | B01L 3/5021 | |
| 10,687,750 B2 * | 6/2020 | Schuetz | A61M 1/3496 | |
| 10,702,629 B2 * | 7/2020 | Pilkington | A61K 35/35 | |
| 10,729,827 B2 * | 8/2020 | Jessop | A61M 1/0094 | |
| 10,772,997 B2 * | 9/2020 | Shippert | A61M 1/008 | |
| 2002/0010405 A1 * | 1/2002 | Hung | A61M 3/0279 | 600/573 |
| 2002/0179537 A1 * | 12/2002 | Sukavaneshvar | A61L 24/0005 | 210/723 |
| 2005/0205498 A1 * | 9/2005 | Sowemimo-Coker | A61L 27/3616 | 210/782 |
| 2005/0250204 A1 * | 11/2005 | Antwiler | B04B 5/0442 | 435/372 |
| 2006/0064070 A1 * | 3/2006 | Martin | B65B 3/003 | 604/403 |
| 2006/0093527 A1 * | 5/2006 | Buss | A61M 1/0084 | 422/501 |
| 2007/0100277 A1 * | 5/2007 | Shippert | A61M 1/00 | 604/27 |
| 2007/0106213 A1 * | 5/2007 | Spera | A61M 31/00 | 604/96.01 |

(56) References Cited

U.S. PATENT DOCUMENTS

| | | | |
|---|---|---|---|
| 2007/0225686 A1* | 9/2007 | Shippert | A61M 1/0001 604/542 |
| 2008/0014181 A1* | 1/2008 | Ariff | C12M 45/05 424/93.7 |
| 2008/0081367 A1* | 4/2008 | Sowemimo-Coker | A61K 35/35 435/325 |
| 2008/0154240 A1* | 6/2008 | Shippert | A61M 1/0056 604/542 |
| 2009/0239299 A1* | 9/2009 | Buss | A61M 1/0084 435/374 |
| 2009/0287190 A1* | 11/2009 | Shippert | A61M 1/0056 604/542 |
| 2009/0294385 A1* | 12/2009 | Tajima | B01D 61/145 210/808 |
| 2010/0137841 A1* | 6/2010 | Khouri | A61M 1/008 604/542 |
| 2010/0279405 A1* | 11/2010 | Peterson | A61K 35/35 435/366 |
| 2010/0317099 A1* | 12/2010 | Leach | B04B 3/00 435/325 |
| 2011/0020196 A1* | 1/2011 | Grippi | B01D 33/15 422/535 |
| 2011/0062153 A1* | 3/2011 | Wang | C02F 1/002 220/23.86 |
| 2011/0130714 A1* | 6/2011 | Wells | A61M 1/0058 604/28 |
| 2011/0183406 A1 | 7/2011 | Kensy | |
| 2012/0037563 A1* | 2/2012 | Liao | B01L 3/502 210/634 |
| 2012/0209248 A1* | 8/2012 | Gurtner | A61M 1/0031 604/506 |
| 2012/0259311 A1* | 10/2012 | Hirshberg | A61B 18/04 604/506 |
| 2012/0277698 A1* | 11/2012 | Andrew | A61M 1/0058 604/319 |
| 2013/0030322 A1* | 1/2013 | Levine | A61B 10/0283 600/566 |
| 2013/0087643 A1* | 4/2013 | Tremolada | C12M 45/02 241/24.1 |
| 2013/0123747 A1* | 5/2013 | Tremolada | A61K 35/35 604/506 |
| 2013/0261606 A1* | 10/2013 | Andrew | A61B 17/3203 604/542 |
| 2014/0021147 A1* | 1/2014 | Leach | B04B 5/0442 210/781 |
| 2014/0081237 A1* | 3/2014 | Wolters | A61M 1/0056 604/506 |
| 2014/0110356 A1* | 4/2014 | McKay | A61F 2/28 210/780 |
| 2014/0130936 A1* | 5/2014 | Shippert | A61M 1/007 141/2 |
| 2014/0188039 A1* | 7/2014 | Andrew | A61M 1/0084 604/28 |
| 2014/0207103 A1* | 7/2014 | Wolters | G01N 1/4044 604/506 |
| 2014/0255356 A1 | 9/2014 | Victor | |
| 2015/0231641 A1* | 8/2015 | Tremolada | A61M 19/00 424/93.7 |
| 2015/0374888 A1* | 12/2015 | Shippert | A61M 1/0001 604/542 |
| 2016/0106353 A1* | 4/2016 | Schuetz | B01D 71/024 210/321.6 |
| 2016/0193429 A1* | 7/2016 | Gurtner | A61M 1/0031 604/28 |
| 2016/0333305 A1* | 11/2016 | Pilkington | A61M 1/00 |
| 2016/0354595 A1* | 12/2016 | Gallagher | A61M 1/0066 |
| 2017/0000969 A1* | 1/2017 | Tremolada | A61M 1/0094 |
| 2017/0002323 A1* | 1/2017 | Tremolada | A61K 35/35 |
| 2017/0021150 A1* | 1/2017 | Hirshberg | A61M 37/0015 |
| 2017/0049942 A1* | 2/2017 | Conlan | A61M 1/0056 |
| 2017/0203040 A1* | 7/2017 | Conlan | A61M 1/0056 |
| 2017/0292110 A1* | 10/2017 | Simpson | A61B 10/0096 |
| 2017/0368226 A1* | 12/2017 | Pilkington | A61M 5/2448 |
| 2018/0133377 A1* | 5/2018 | Khouri | A61M 1/0009 |
| 2018/0303983 A1* | 10/2018 | Goisis | A61M 1/0056 |
| 2019/0125971 A1* | 5/2019 | Bachrach | A61L 27/3687 |
| 2019/0143005 A1* | 5/2019 | Conlan | A61M 1/0009 604/542 |
| 2019/0185814 A1* | 6/2019 | Bachrach | A61M 1/0056 |
| 2019/0232017 A1* | 8/2019 | Tremolada | A61M 5/002 |
| 2020/0215533 A1* | 7/2020 | Chapman | B01L 3/50 |

FOREIGN PATENT DOCUMENTS

| | | | |
|---|---|---|---|
| IT | 102015902323792 A | 7/2016 | |
| WO | 2006/100651 A1 | 9/2006 | |
| WO | 2015/015471 A2 | 2/2015 | |
| WO | 2015/071852 A2 | 5/2015 | |
| WO | WO-2017064656 A1 * | 4/2017 | A61M 1/029 |

* cited by examiner

FAT FILTRATION DEVICE

CROSS REFERENCE TO RELATED APPLICATIONS

The present application is the U.S. National Stage of International Patent Application No. PCT/IB2016/056157 filed on Oct. 14, 2016 which, in turn, claims priority to Italian Patent Application No. 102015000061679 filed on Oct. 14, 2015.

TECHNICAL FIELD OF THE INVENTION

The present invention generally relates to aesthetic medicine and surgery and in particular to a device for the filtration of fat extracted by way of surgical liposuction procedures.

BACKGROUND

Liposuction has been introduced since the 70s of the last century. Initially it was a very invasive intervention carried out under general anesthesia in major surgery rooms. The procedure took several hours and fat in excess was sucked by way of large cannulas with a diameter ranging from 1 to 4 cm connected to a high-power suction unit. The fat was then eliminated along with large amounts of blood and anesthetic. In many cases, blood transfusions were required in the days following an intervention and many complications and deaths are reported in medical literature.

Less invasive liposuction techniques have been developed only since the 90s of the last century. The size of the cannulas has been progressively reduced up to diameters of 2-5 mm. The introduction of the tumescent anesthesia technique has allowed to carry out surgical interventions under local anesthesia. According to the tumescent technique a large volume of liquid containing a local anesthetic combined with a vasoconstrictor (adrenaline) is injected in an area to be treated. This injection reduces the pain caused to the patient during suction of fat and allows to limit bleeding, thus making liposuction easier and less dangerous.

The so-called "lipofilling" procedures have been developed over the past 20 years. These procedures exploit the sucked fat as a filler to reshape and increase of the volume of breast, gluteus and calf. Face wrinkles may also be filled and corrected, lips, cheekbones and chin may be reshaped as well.

Therefore it has become necessary to preserve the integrity of the sucked fat as much as possible. Unlike the first liposuction procedures, in fact, fat is no longer eliminated, but becomes a resource in the frame of the aesthetic procedure. The effectiveness of this resource is closely related to the survival of fat cells, i.e. adipocytes and stem cells and adipocyte precursor cells. These cells are taken from a site where they are in excess (thighs, abdomen, hips) and are grafted on a site to be reshaped (breasts, lips, etc.). The procedure is very delicate and is always accompanied by the death of a variable percentage of adipocytes. The survival rate ranges between 70%, in the better cases, and below 10%, which means failure of the lipofilling procedure.

The survival of fat cells is linked to several factors, such as their individual properties, the degree of oxidation of the tissues, the type of infiltration technique, the fact that the patient is a smoker, the trauma caused by a cannula during the sucking process, etc. The local anesthetic used to numb the surgical site is among the most important damaging factors for the adipocytes, because it has a toxic effect on the cells in the 12-24 hours subsequent to their graft into the target site. Damage is increased by the presence of erythrocytes that have an important oxidative effect if left with fat cells. In order to reduce tissue damage cannulas of a smaller size have recently been developed. These cannulas can be more easily inserted in the fatty tissue thus reducing the force to be applied. Cannulas having special patterns and shape of the holes through which fat is sucked have also been developed. An example of such cannulas is described in the Italian patent application no. 102015902323792 in the applicant's name.

During a liposuction procedure it is necessary to inject an anesthetic solution into the site from which fat has to be sucked. The anesthetic is usually injected by way of syringes.

Once made the anesthesia, suitable liposuction cannulas are mounted on the same syringes employed for this purpose and used to suck fat. The sucked fat is mixed with local anesthetic and blood. The difference in specific gravity is usually exploited as a means to separate adipocyte cells from the liquid mixture. To this aim the syringes are kept vertically manually or by way of suitable racks. Fat has a lower specific gravity and is collected in the upper part of a syringe, i.e. towards the plunger, while the liquid mixture is deposited in the lower part of the syringe, wherein an attachment member of the cannula is arranged, and can thus be eliminated.

In order to ensure survival of adipocyte cells in view of a subsequent lipofilling procedure, the fat remaining in the syringe must be processed with a washing solution, typically a physiological solution, for one or more cycles so as to purify it from residual blood and anesthetic. Blood and anesthetic are in fact toxic to adipocytes. More particularly, in each cycle a certain amount of washing solution is sucked into the syringe, which is then positioned vertically so as to allow separation of fat and liquid, the latter consisting of physiological solution, residual blood and anesthetic. The liquid deposited in the lower part of the syringe because of its higher specific gravity is then eliminated and fresh physiological solution is sucked into the syringe so as to carry out another washing and separation cycle.

A number of different containers are generally employed for the above operations, whose success is highly dependent on the manual ability of an operator. The containers must be properly prepared and organized before surgery. For example, a first container is filled with physiological or saline solution, a second container is filled with an anesthetic and a third container is used to collect the liquid to be eliminated at each cycle of the purification process. These containers are generally open and thus exposed to a possible contamination by bacteria present in an operating room.

SUMMARY OF THE INVENTION

The technical problem posed and solved by the present invention is to improve purification procedures of the fat extracted by liposuction, with particular reference to devices employed in the purification procedures.

The invention consists in a filtration device comprising a filter element on one side of which a connection member is arranged allowing to connect a syringe containing fat extracted from a patient during a liposuction procedure. The syringe also contains a liquid mixture consisting of blood and anesthetic that are sucked with the fat. On the opposite side of the filter element a first reservoir containing a physiological solution and a second, empty reservoir are connected in parallel by way of a three-way connector. The filter element is configured to hold fat cells and let the liquid mixture pass.

The filtration device is configured such that by injecting the content of the syringe towards the filter element, the liquid mixture crossing it is directed to and collected in the second, empty reservoir, whereas by operating the plunger of the syringe in the opposite direction, washing solution is sucked from the first reservoir through the filter element. The washing solution is then mixed with the fat and the residues contained in the syringe. An assembly of one-way valves, taps and/or filters ensures tightness of the device, resulting in a reduction of the contamination and subsequent infection risks.

Therefore, by cyclically repeating the injection and suction steps, the fat contained in the syringe is progressively purified from residues of blood and anesthetic.

The main advantage offered by the invention is therefore to provide a surgeon with a filtration device for fat (formed by adipocytes, adipocyte precursors and stem cells) that, thanks to the provision of a filter element, allows to carry out in a reliable and repeatable way all the operations that are typically performed manually by using individual containers. Subsequent lipofilling procedures employing the fat so purified have greater chances of success than procedures employing fat purified by known methods.

Another important advantage offered by the invention is that the fat purification procedure is simpler and faster than procedures carried out according to the prior art.

According to an embodiment of the invention, the filtration device is configured so as to allow connection of a plurality of syringes in parallel, thus advantageously allowing to treat larger quantities of fat. To this aim, a duct provided with a plurality of attacks that are selectively accessible for the mounting of a plurality of respective syringes is connected to the filter element.

A further filter element may be connected to the duct, as well as a three-way connector for the connection of a further reservoir containing physiological solution and a further, empty reservoir for collecting the liquid mixture separated from the fat, both reservoirs being arranged on the opposite side of the further filter element. This configuration provides the additional advantage of improving the filtration device, which can thus purify an even larger amount of fat.

The liquid mixture collected in the second reservoir typically has disposal problems, because it has an organic content that is mainly liquid and undergoes a rapid degradation resulting in unpleasant odors. According to an embodiment of the invention, an element made of or comprising an absorbent material can be advantageously arranged in the second reservoir so as to allow easier disposal of the liquid mixture.

Further advantages and features of the filtration device according to the present invention will become clear to those skilled in the art from the following detailed and non-limiting description of embodiments thereof, with reference to the accompanying drawings.

BRIEF DESCRIPTION OF THE DRAWINGS

Reference will be made to the figures of the accompanying drawings, in which.

DETAILED DESCRIPTION OF PREFERRED EMBODIMENTS OF THE INVENTION

Figure 1:
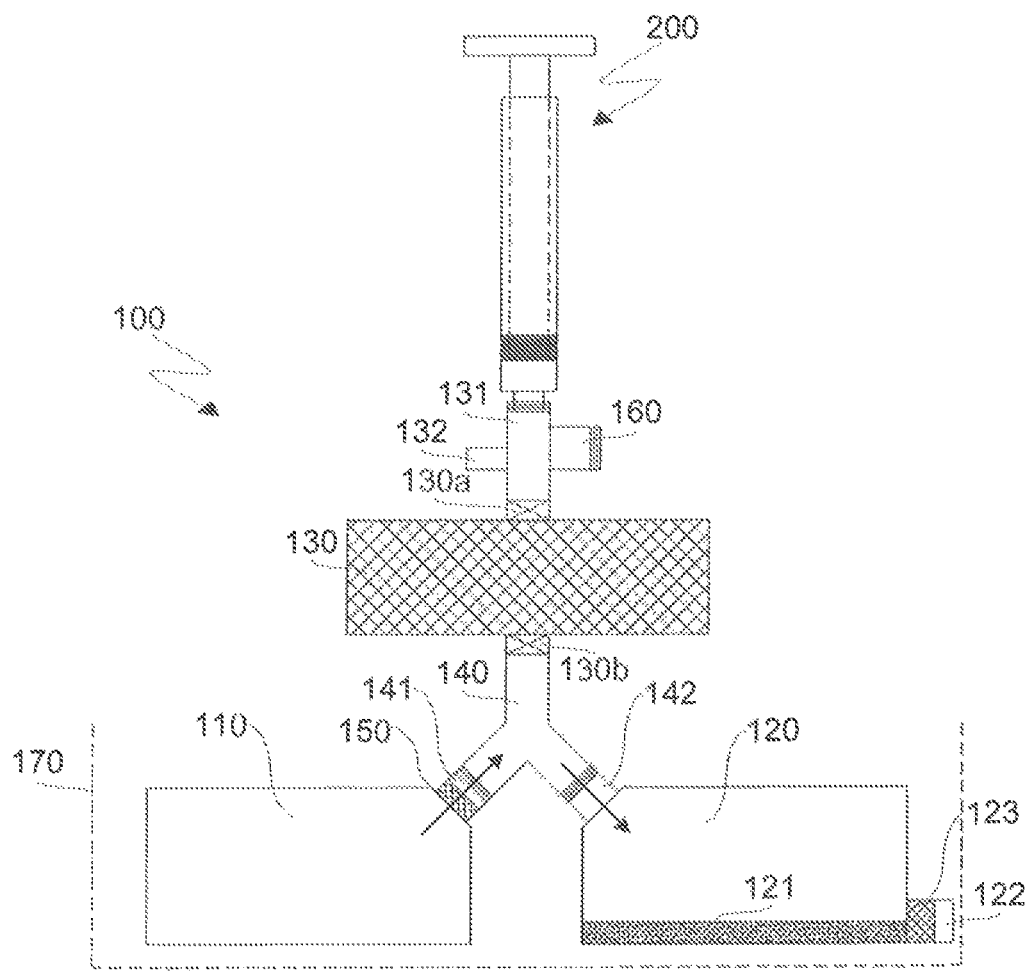
FIG. 1 schematically shows a filtration device according to an embodiment of the invention.

With reference to FIG. 1, a filtration device according to the invention is generally indicated by reference numeral 100 and comprises a first reservoir 110, in the form of a receptacle, container or bag, filled with a washing solution adapted to be sucked by a syringe 200 containing a certain amount of fat mixed with blood and anesthetic. The filtration device 100 further comprises a second, empty reservoir 120 intended to cyclically receive from the syringe 200 a liquid mixture consisting of the sucked washing solution and of the blood and anesthetic separated from the fat.

The device 100 also comprises a least one filter element 130 connected on one side to the first reservoir 110 and to the second reservoir 120 through a three-way connector 140. A one-way valve 141 is arranged on the branch of the connector 140 connected to the first reservoir 110. The one-way valve 141 is configured to allow passage of a fluid flow, in this case washing solution, from the first reservoir 110 to the connector 140. On the branch of the connector 140 connected to the second reservoir 120 a one-way valve 142 is arranged. The one-way valve 142 is configured to allow passage of a fluid flow, in this case the washing solution together with blood and anesthetic, from the connector 140 toward the second reservoir 120. Flow directions are schematically shown in FIG. 1 by arrows.

A connection member 131 is arranged on the side of the filter element 130 opposite to the side to which the first and second reservoirs 110, 120 are connected. The connection member 131, such as e.g. a standard "luer-lock" attack, is configured to allow connection of the syringe 200.

The filter element 130 is configured to hold fat cells and/or stem cells and adipose tissue precursors and let the liquid mixture pass. To this aim the filter element 130 includes meshes with apertures having a size ranging between 10 and 200 microns, preferably between 15 and 100 microns. The filter element 130 can be made up of a number of filters having a different mesh size in order to optimize the filtration process. For the same purpose a plurality of filter elements 130 may also be arranged in series.

In the figures, the junctions zones between the various components of the device are schematically indicated by hatching with parallel lines, and may advantageously comprise shut-off and flow control valves, for example taps. For instance, two taps 130a, 130b are arranged at the opposite ends of the filter 130 and respectively attached to the connection member 131 and to the connector 140.

In order to carry out a purification procedure of fat sucked into the syringe 200 in view of a lipofilling procedure, the syringe is mounted on the connection member 131 and its entire content is injected into the filter element 130 by acting on the plunger. Fat cells are held by the filter element 130, which instead lets the liquid mixture consisting of washing solution, blood and anesthetic pass. More particularly, blood consists of a liquid component, the plasma, and of a corpuscular component having small size elements. The average diameter of red and white blood cells is in fact comprised between 5 and 12 microns. The liquid component and the blood enter the three-way connector 140 and are collected in the second reservoir 120 after crossing the one-way valve 142. As explained above, it will be understood that in this phase the one-way valve 141 prevents entry of the liquid mixture and of the blood into the first reservoir 110.

By operating the plunger of the syringe 200 in the opposite direction, namely by pulling it from the syringe body, the one-way valve 142 of the connector 140 is closed, whereas the one-way valve 141 is opened thus allowing suction of washing solution from the first reservoir 110 through the filter element 130. Fat is thus mixed inside the syringe 200 with the washing solution coming from the first reservoir 110.

The syringe 200 so filled with fat and washing solution is again discharged as explained above thus carrying out a new purification cycle of the fat, which is held by the filter element 130 purified from the liquid mixture, this time consisting of washing solution and residues of blood and anesthetic.

Further purification cycles are then carried until the fat sucked into the syringe is completely free from residues of blood and anesthetic, and is therefore in the ideal condition to be used in a subsequent lipofilling procedure.

In order to ensure the best outcome of a purification procedure, the device 100 according to the invention may advantageously comprise a microfilter 150 arranged between the first reservoir 110 and the one-way valve 141 connecting it to the connector 140. The microfilter 150, e.g. provided with meshes with a passage size in the order of fractions of a micron (0.2 micron for example), allows to retain any impurities and bacteria present in the washing solution sucked into the syringe 200, which would otherwise be mixed with the fat.

Still in the aim to ensure the best outcome of a purification procedure, the device 100 may also advantageously comprise a safety valve calibrated to be opened beyond a predetermined pressure threshold.

The safety valve, schematically indicated with the reference number 160, is connected in a branch configuration to the connection member 131 of the filter element 130.

The use of a safety valve allows to limit the maximum injection pressure of the fat towards the filter element 130, and therefore to limit the mechanical compression of fat cells against its meshes, thus ensuring higher chances of survival during a purification procedure. The possible portion of fat and liquid mixture discharged through the safety valve 160 may be collected into a container (not shown) connected thereto, or, more advantageously, into a further syringe (not shown). In this way, the fat collected into the additional syringe may be reintroduced into the device and will not be lost.

The safety valve 160 may be advantageously associated with a pressure sensor (not shown) provided with a visual and/or sound indicator, which allows a user to reduce the pressure exerted on the plunger of the syringe 200 in case the predetermined pressure threshold is exceeded. After washing, residues of fat possibly present in the filter can be collected in a container (not shown) connected thereto or, more advantageously, in a further syringe (not shown). In this way, the fat present in the filter and in the device will not be lost.

Still in order to ensure the best outcome of the purification procedure and to minimize loss of fat in the device 100, this may also advantageously comprise two taps arranged immediately above and immediately below the filter 130, as well as a third tap equipped with a luer-lock or similar attack.

According to a further aspect of the invention, the second reservoir 120 may comprise an element 121 made of or comprising an absorbent material. In this way, washing liquid and blood can be eliminated in a simpler and faster way. According to an embodiment of the invention, the element made of an absorbent material is contained in a film of a water-soluble material, in turn enclosed in a disposable envelope, as described in the patent publication EP 2452660 A1.

A sensor 132 adapted to measure the relative percentages of fat and washing solution may be advantageously connected to the connection member 131. The sensor may e.g. include an electrical impedance, an infrared measuring device of the type NIR (Near-Infrared Interactance), an electromagnetic field generator of the type TOBEC (Total Body Electrical Conductivity), or an x-ray system of the type DEXA (Dual Energy X-Ray Absorptiometry).

The device 100 according to the invention may advantageously be placed on a scale 170, schematically shown in dashed lines, e.g. arranged under the first and the second reservoirs 110, 120 for measuring the weight of the amount of fat and liquid mixture sucked from a patient and intended to be purified.

According to a further aspect of the invention, the second reservoir 120 may include an outlet 122 configured for the discharge of the liquid mixture. The outlet 122 is preferably disposed proximate to the bottom of the second reservoir 120 so as to facilitate its emptying. A filter element 123 configured for the filtration of specific cellular elements which pass through the filter element 130 together with the liquid mixture may be advantageously associated with the outlet 122, The filter element 123 may for example have passages with a size in the order of 12-180 microns.

Figure 2:
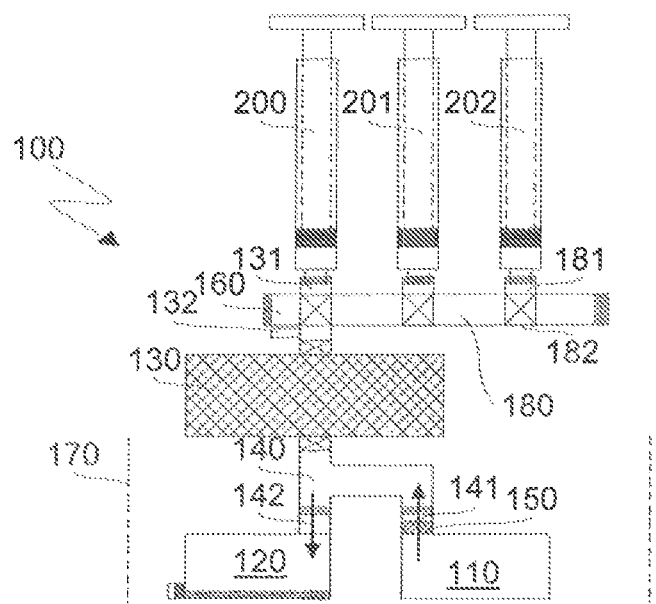
FIG. 2 schematically shows a filtration device according to an alternative embodiment of the invention.

Now referring to FIG. 2, an alternative embodiment of the device 100 according to the present invention is disclosed, the device being configured so as to allow connection in parallel of a plurality of syringes.

Similarly to the first embodiment of the invention, also in this case the device 100 comprises a first reservoir 110, i.e. a receptacle, a container or a bag (hereinafter named reservoir) filled with a washing solution and a second, empty reservoir 120, i.e. a receptacle, a container or a bag (hereinafter named reservoir), intended to cyclically receive from the syringe 200 a liquid mixture consisting of the sucked washing solution, blood and anesthetic separated from the fat.

The device 100 also comprises a filter element 130 connected on one side thereof to the first reservoir 110 and to second reservoir 120 through a three-way connector 140. A one-way valve 141 configured to allow passage of washing solution from the first reservoir 110 to the connector 140 is arranged on the branch of the connector 140 connected to the first reservoir 110. On the branch of the connector 140 connected to the second reservoir 120 a one-way valve 142 configured to allow passage of the washing solution, blood and anesthetic, from the connector 140 toward the second reservoir 120 is arranged. The flow directions are schematically shown in FIG. 2 by means of arrows.

A connection member 131 configured for the connection of the syringe 200 is arranged on the opposite side of the filter element 130. The connection member 131 may be e.g. a standard "luer-lock" attack.

In order to allow mounting in parallel of a plurality of syringes 200, the device 100 also includes a duct 180 connected in a branch configuration to the connection member 131 of the filter element 130. The duct 180 is arranged in fluid communication with the connection member 131 and comprises a plurality of mounts 181, for example of the "luer-lock" type, that are selectively accessible so as to connect respective syringes in parallel, e.g. a second syringe 201 and a third syringe 202. Each syringe can inject its content into the filter element 130, suck physiological solution from the first reservoir 110 and discharge the liquid mixture separated from the fat into the second reservoir 120. In other words, the overall configuration of the device 100 is such that all the syringes can perform in parallel the purification procedure of the fat they contain by using the first and the second reservoirs 110, 120 as described above. Taps 182, for example three-way taps of the type "Stopcoks", may advantageously be arranged in the duct 180 in correspondence with each syringe mount. The taps 182 allow to selectively adjust the flow of fat and liquid mixture within the device 100.

Figure 3:
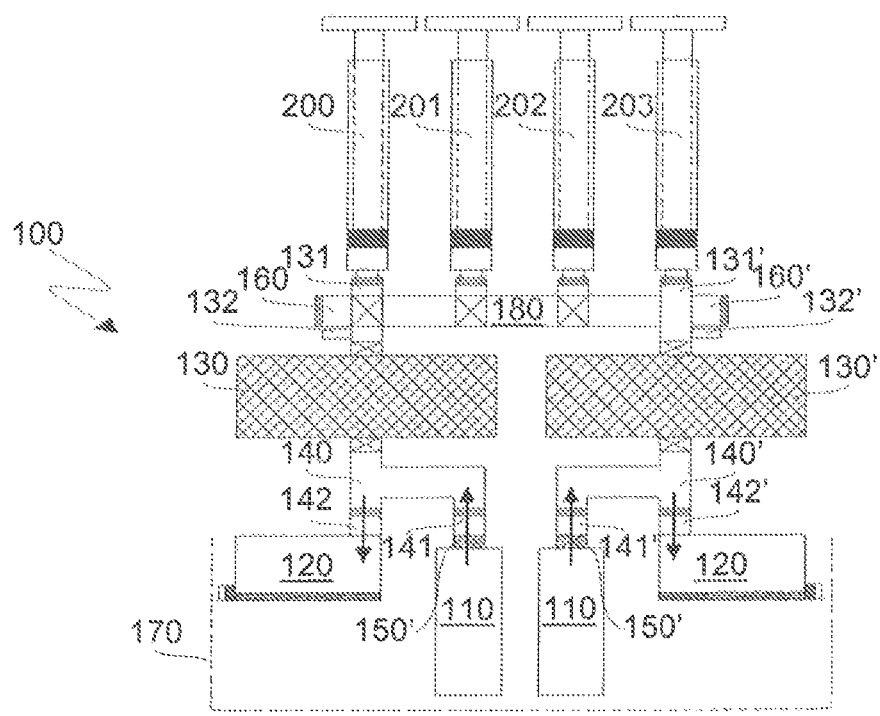
FIG. 3 schematically shows a filtration device according to a further embodiment of the invention.

According to a further embodiment of the invention, shown in FIG. 3, the device 100 is configured for the connection of a plurality of syringes as described above, and may advantageously comprise a further filter element 130' provided with a respective connection member 131' connected to the duct 180 and configured for the connection of a further syringe 203, as well as a possible further first reservoir 110' filled with a physiological solution and a possible further second, empty reservoir 120' intended to receive the liquid mixture separated from the fat. The second reservoir 120' may possibly be provided with an element 121' made of or comprising an absorbing material.

Similarly to the embodiments described above, the attack 131' may be associated with a safety valve 160', as well as with a sensor 132' adapted to measure the relative percentages of fat and washing solution.

Moreover, the further first and second reservoirs 110', 120' are connected to the further filter element 130' through a three-way connector 140' and one-way valves 141', 142' that are respectively configured to allow passage of physiological solution from the first reservoir 110' to the connector 140' and from the connector 140' to the second reservoir 120'.

This configuration of the filtration device 100 allows to increase the amount of fat contained in the syringes arranged in parallel that can be subjected to the purification procedure.

The invention has herein been disclosed with reference to preferred embodiments thereof. It is to be understood that there may be other embodiments based on the same inventive concept, as defined by the scope of protection of the claims set out below.

The invention claimed is:

1. A filtration device comprising:
   a first syringe including a plunger and a syringe body;
   a filter having a first and a second connection member;
   a three-way connector having three branches for connection;
   a first one-way valve;
   a second one-way valve;
   a first reservoir having a connection port;
   a second reservoir having a connection port;
   wherein said first syringe is fluidically connected to said first connection member of said filter, while said second connection member of said filter is fluidically connected to a branch of said three-way connector, with said first and second reservoirs being fluidically connected to the two other branches of the three-way connector with said first and second one-way valves respectively being situated in the flowpaths defined by such connections in a manner that only permits fluid flow out of said first reservoir when said plunger of said syringe is withdrawn from the syringe body and only permits fluid flow into said second reservoir when said plunger of said syringe is forcibly inserted into said syringe body.

2. The filtration device according to claim 1, wherein the filter comprises a mesh with passages of a size between 10 and 200 microns.

3. The filtration device according to claim 2, wherein the size of the passages is between 15 and 70 microns.

4. The filtration device according to claim 1, further comprising a microfilter fluidically arranged between said first reservoir and said first one-way valve.

5. The filtration device according to claim 4, wherein said microfilter has an aperture size of 0.2 microns.

6. The filtration device according to claim 1, further comprising a safety valve calibrated to open when a predetermined pressure threshold is reached, said safety valve being fluidically connected in a branch configuration to said first connection member of the filter.

7. The filtration device according to claim 6, wherein the safety valve comprises a pressure sensor provided with a visual and/or audible indicator.

8. The filtration device according to claim 1, further comprising a duct fluidically connected in a branch configuration to the first connection member of said filter, said duct being provided with a plurality of mounts for selectively mounting additional syringes in parallel to said first syringe.

9. The filtration device according to claim 8, further comprising at least one additional filter provided with a respective syringe connection member fluidically connected to said duct, as well as at least one additional first reservoir and at least one additional second reservoir, said additional first and second reservoirs being connected to said at least one additional filter on a side opposite the side on which said syringe connection member is arranged.

10. The filtration device according to claim 9, wherein said additional first and second reservoirs are connected to said at least one additional filter through a three-way connector and one-way valves fluidically connected in such a way to only allow passage of a flow of fluid from said additional first reservoir towards the three-way connector and from the three-way connector towards said additional second reservoir.

11. The filtration device according to claim 1, wherein said first connection member comprises a sensor including at least one of an electrical impedance measuring device, an infrared measuring device, an electromagnetic field generator, and/or an X-ray system.

12. The filtration device according to claim 1, wherein the second reservoir includes an absorbent material.

* * * * *